United States Patent [19]

Stetter et al.

[11] Patent Number: 4,799,951
[45] Date of Patent: Jan. 24, 1989

[54] 5-ACYLAMINO-PYRAZOLE DERIVATIVES, COMPOSITION CONTAINING THEM AND HERBICIDAL METHOD OF USING THEM

[75] Inventors: Jörg Stetter, Wuppertal; Otto Schallner, Monheim; Reinhold Gehring, Wuppertal; Hans-Joachim Santel, Leverkusen; Robert R. Schmidt, Bergisch Gladbach; Klaus Lürssen, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 113,298

[22] Filed: Oct. 26, 1987

[30] Foreign Application Priority Data

Nov. 5, 1986 [DE] Fed. Rep. of Germany ....... 3637710

[51] Int. Cl.$^4$ .................. A01N 43/56; C07D 231/40
[52] U.S. Cl. ........................................ 71/92; 546/279; 548/362; 548/376; 548/377; 71/72; 71/74
[58] Field of Search ................ 546/279; 548/362, 376, 548/377; 71/92

[56]  References Cited

FOREIGN PATENT DOCUMENTS 0154115  9/1985  European Pat. Off. ................ 71/92
0207285  1/1987  European Pat. Off. ................ 71/92
3226513  2/1983  Fed. Rep. of Germany .......... 71/92

OTHER PUBLICATIONS

Chemical Abstracts, vol. 61, No. 13, Dec. 21, 1964, 16061.

Primary Examiner—Mary C. Lee
Assistant Examiner—Kurt G. Briscoe
Attorney, Agent, or Firm—Sprung Horn Kramer & Woods

[57]  ABSTRACT

Herbicidal 5-acylamino-pyrazole derivatives of the formula

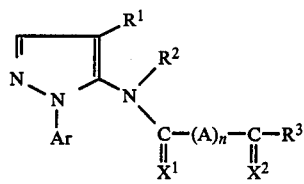

in which
$R^1$ represents hydrogen, halogen or nitro,
$R^2$ represents hydrogen, alkyl, alkenyl, alkinyl or optionally substituted cycloalkyl,
$R^3$ represents hydrogen or alkyl, or represents optionally substituted cycloalkyl, or represents optionally substituted aryl,
Ar represents in each case optionally substituted phenyl or pyridyl,
$X^1$ represents oxygen or sulphur,
A represents a straight-chain or branched optionally substituted alkylene bridge,
n represents the number 0 to 1 and
$X^2$ represents oxygen, or represents a radical $=N-O-R^4$, or represents a radical

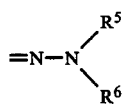

wherein
$R^4$ represents hydrogen, alkyl, alkenyl, alkinyl, halogenoalkyl, halogenoalkenyl, alkoxyalkyl or alkylthioalkyl, or represents optionally substituted aralkyl, or represents optionally substituted aryl,
$R^5$ represents hydrogen or alkyl and
$R^6$ represents hydrogen or alkyl, or represents optionally substituted aryl, or represents a radical

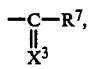

wherein
$X^3$ represents oxygen or sulphur and
$R^7$ represents hydrogen, alkyl, alkoxy, alkylamino or dialkylamino.

9 Claims, No Drawings

5-ACYLAMINO-PYRAZOLE DERIVATIVES, COMPOSITION CONTAINING THEM AND HERBICIDAL METHOD OF USING THEM

The invention relates to new 5-acylamino-pyrazole derivatives, several processes for their preparation and their use as herbicides and growth regulators.

It is already known that certain 5-acylamino-1-aryl-pyrazoles, such as, for example, 4-cyano-5-propionamido-1-(2,4,6-trichlorophenyl)-pyrazole, have herbicidal properties (compare, for example, DE-OS (German Published Specification No. 3,226,513).

However, the herbicidal activity of these already known compounds against weeds, like their tolerance towards important crop plants, is not always completely satisfactory in all fields of use.

New 5-acylamino-pyrazole derivatives of the general formula (I)

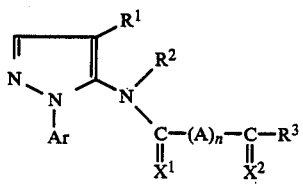

in which
$R^1$ represents hydrogen, halogen or nitro,
$R^2$ represents hydrogen, alkyl, alkenyl, alkinyl or optionally substituted cycloalkyl,
$R^3$ represents hydrogen or alkyl, or represents optionally substituted cycloalkyl, or represents optionally substituted aryl,
Ar represents in each case optionally substituted phenyl or pyridyl,
$X^1$ represents oxygen or sulphur,
A represents a straight-chain or branched optionally substituted alkylene bridge,
n represents the number 0 or 1 and
$X^2$ represents oxygen, or represents a radical $=N-O-R^4$, or represents a radical

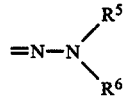

wherein
$R^4$ represents hydrogen, alkyl, alkenyl, alkinyl, halogenoalkyl, halogenoalkenyl, alkoxyalkyl or alkylthioalkyl, or represents optionally substituted aralkyl, or represents optionally substituted aryl,
$R^5$ represents hydrogen or alkyl and
$R^6$ represents hydrogen or alkyl, or represents optionally substituted aryl, or represents a radical

wherein
$X^3$ represents oxygen or sulphur and
$R^7$ represents hydrogen, alkyl, alkoxy, alkylamino or dialkylamino, have been found.

It has furthermore been found that the new 5-acylamino-pyrazole derivatives of the formula (I)

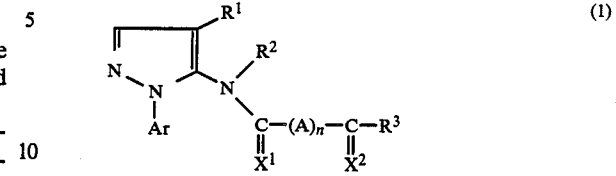

in which
$R^1$ represents hydrogen, halogen or nitro,
$R^2$ represents hydrogen, alkyl, alkenyl, alkinyl or optionally substituted cycloalkyl,
$R^3$ represents hydrogen or alkyl, or represents optionally substituted cycloalkyl, or represents optionally substituted aryl,
Ar represents in each case optionally substituted phenyl or pyridyl,
$X^1$ represents oxygen or sulphur,
A represents a straight-chain or branched optionally substituted alkylene bridge,
n represents the number 0 or 1 and
$X^2$ represents oxygen, or represents a radical $=N-O-R^4$, or represents a radical

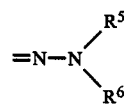

wherein
$R^4$ represents hydrogen, alkyl, alkenyl, alkinyl, halogenoalkyl, halogenoalkenyl, alkoxyalkyl or alkylthioalkyl, or represents optionally substituted aralkyl, or represents optionally substituted aryl,
$R^5$ represents hydrogen or alkyl and
$R^6$ represents hydrogen or alkyl, or represents optionally substituted aryl, or represents a radical

wherein
$X^3$ represents oxygen or sulphur and
$R^7$ represents hydrogen, alkyl, alkoxy, alkylamino or dialkylamino,
are obtained with the aid of the processes described below:

(a) 5-acylamino-pyrazole derivatives of the formula (Ia)

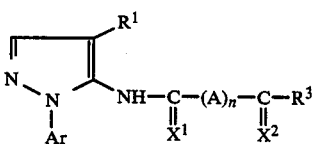

in which
$R^1$, $R^3$, $X^1$, $X^2$, A, Ar and the index n have the above-mentioned meaning,
are obtained by a process in which 5-amino-1-aryl-pyrazoles of the formula (II)

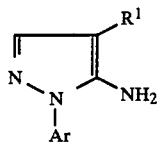 (II)

in which
R$^1$ and Ar have the abovementioned meaning, are reacted with acylating agents of the formula (III)

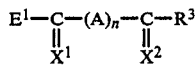 (III)

in which
X$^1$, X$^2$, R$^3$, A and the index n have the above-mentioned meaning and
E$^1$ represents an electron-withdrawing leaving group, if appropriate in the presence of a diluent, if appropriate in the presence of an acid-binding agent and if appropriate in the presence of a catalyst;

(b) 5-acylamino-pyrazole derivatives of the formula (Ib)

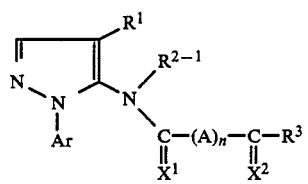 (Ib)

in which
R$^1$, R$^3$, X$^1$, X$^2$, A, the index n and Ar have the above-mentioned meaning and
R$^{2-1}$ represents alkyl, alkenyl, alkinyl or optionally substituted cycloalkyl,
are obtained by a process in which the 5-acylaminopyrazole derivatives obtainable by process (a), of the formula (Ia)

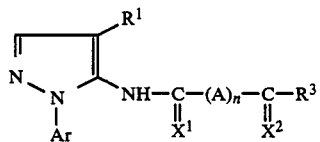 (Ia)

in which
R$^1$, R$^3$, X$^1$, X$^2$, A, Ar and the index n have the abovementioned meaning,
are reacted with alkylating agents of the formula (IV)

 (IV)

in which
R$^{2-1}$ has the abovementioned meaning and
E$^2$ represents halogen, or represents optionally substituted alkoxysulphonyloxy, or represents optionally substituted arylsulphonyloxy,
if appropriate in the presence of a diluent and if appropriate in the presence of an acid-binding agent, and if appropriate in the presence of a catalyst;

(c) 5-acylamino-pyrazole derivatives of the formula (Ic)

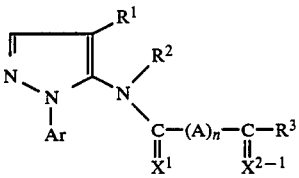 (Ic)

in which
R$^1$, R$^2$, R$^3$, X$^1$, A, Ar and the index n have the abovementioned meaning and
X$^{2-1}$ represents a radical =N—O—R$^4$ or represents a radical

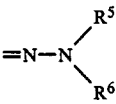

wherein
R$^4$, R$^5$ and R$^6$ have the abovementioned meaning, are obtained by a process in which the 5-acylaminopyrazole derivatives obtainable by process (a) or (b), of the formula (Ie)

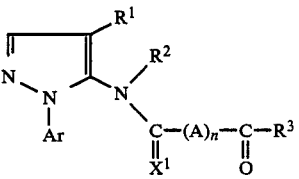 (Ie)

in which
R$^1$, R$^2$, R$^3$, X$^1$, A, Ar and the index n have the abovementioned meaning,
are reacted with primary amino compounds of the formula (V)

 (V)

in which
Y represents a radical —OR$^4$, or represents a

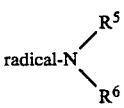

wherein
R$^4$, R$^5$ and R$^6$ have the abovementioned meaning, if appropriate in the presence of a diluent and if appropriate in the presence of a reaction auxiliary;

(d) 5-acylamino-pyrazole derivatives of the formula (Id)

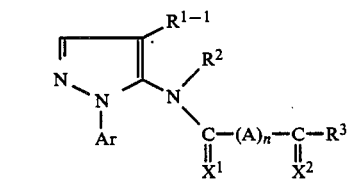 (Id)

in which $R^2$, $R^3$, $X^1$, $X^2$, A, Ar and the index n have the abovementioned meaning and
$R^{1-1}$ represents halogen or nitro,
are obtained by a process in which the 5-acylaminopyrazole derivatives obtainable with the aid of processes (a), (b) or (c), of the formula (If)

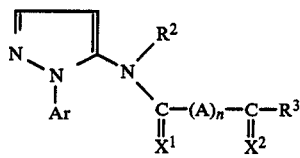

in which
$R^2$, $R^3$, $X^1$, $X^2$, A, Ar and the index n have the abovementioned meaning,
are reacted with halogenating or nitrating agents of the formula (VI)

 (VI)

in which
$R^{1-1}$ has the abovementioned meaning and
$E^3$ represents an electron-withdrawing leaving group, if appropriate in the presence of a diluent and if appropriate in the presence of a catalyst or reaction auxiliary.

Finally, it has been found that the new 5-acyl-aminopyrazole derivatives of the general formula (I) have herbicidal properties, and in particular also selective herbicidal and growth-regulating properties.

Surprisingly, the 5-acylamino-pyrazole derivatives of the general formula (I) according to the invention exhibit a considerably better general herbicidal activity against problem weeds which are difficult to combat and at the same time a significantly improved tolerance towards important crop plants in comparison with the 5-acylamino-1-arylpyrazoles known from the prior art, such as, for example, 4-cyano-5-propionamido-1-(2,4,6-trichlorophenyl)-pyrazole, these being closely related compounds chemically and from the point of view of their action.

Formula (I) provides a general definition of the 5-acylamino-pyrazole derivatives according to the invention. Preferred compounds of the formula (I) are those in which
$R^1$ represents hydrogen, nitro, fluorine, chlorine, bromine or iodine,
$R^2$ represents hydrogen, or represents straight-chain or branched alkyl with 1 to 12 carbon atoms, or represents in each case straight-chain or branched alkenyl or alkinyl with in each case 3 to 8 carbon atoms, or represents cycloalkyl which has 3 to 8 carbon atoms and is optionally mono- or polysubstituted by identical or different $C_1$-$C_4$-alkyl radicals,
$R^3$ represents hydrogen, or represents straight-chain or branched alkyl with 1 to 8 carbon atoms, or represents cycloalkyl which has 3 to 8 carbon atoms and is optionally monosubstituted or polysubstituted by identical or different $C_1$-$C_4$-alkyl radicals, or represents aryl which has 6 to 10 carbon atoms and is optionally monosubstituted or polysubstituted by identical or different substituents, possible substituents on the aryl being: halogen, cyano, nitro and in each case straight-chain or branched alkyl and alkoxy with in each case 1 to 4 carbon atoms,
Ar represents phenyl, 2-pyridyl, 3-pyridyl or 4pyridyl, in each case optionally monosubstituted or polysubstituted by identical or different substituents, possible substituents in each case being: halogen, cyano, nitro, in each case straight-chain or branched alkyl, alkoxy and alkoxycarbonyl with in each case 1 to 4 carbon atoms in the alkyl part, in each case straight-chain or branched halogenoalkyl and halogenoalkoxy with in each case 1 to 4 carbon atoms and 1 to 9 identical or different halogen atoms, and a radical —$S(O)_m$—$R^8$,
wherein
$R^8$ represents amino, or represents in each case straight-chain or branched alkyl, alkylamino, dialkylamino or halogenoalkyl with in each case 1 to 4 carbon atoms in the individual alkyl parts and, in the case of halogenoalkyl, with 1 to 9 identical or different halogen atoms and
m represents the number 0, 1 or 2,
$X^1$ represents oxygen or sulphur,
A represents a straight-chain or branched alkylene bridge which has 1 to 6 carbon atoms and is optionally monosubstituted or polysubstituted by identical or different substituents from the group comprising phenyl, which is optionally monosubstituted or polysubstituted by identical or different halogen or $C_1$-$C_4$-alkyl radicals, and halogen,
n represents the number 0 or 1 and
$X^2$ represents oxygen, or represents a radical =N—O—$R^4$, or represents a radical

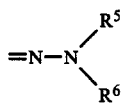

wherein
$R^4$ represents hydrogen, or represents straight-chain or branched alkyl with 1 to 8 carbon atoms, or represents in each case straight-chain or branched alkenyl or alkinyl with in each case 3 to 8 carbon atoms, or represents in each case straight-chain or branched halogenoalkyl with 1 to 8 carbon atoms or halogenoalkenyl with 3 to 8 carbon atoms and in each case 1 to 9 identical or different halogen atoms, or represents in each case straight-chain or branched alkoxyalkyl or alkylthioalkyl with in each case 1 to 4 carbon atoms in the individual alkyl parts, or represents aralkyl with 1 to 4 carbon atoms in the alkyl part or aryl, with in each case 6 to 10 carbon atoms in the aryl part and in each case monosubstituted or polysubstituted by identical or different substituents in the aryl part, possible substituents on the aryl in each case being: halogen, cyano, nitro and in each case straight-chain or branched alkyl or alkoxy with in each case 1 to 4 carbon atoms,
$R^5$ represents hydrogen, or represents straight-chain or branched alkyl with 1 to 6 carbon atoms and
$R^6$ represents hydrogen, or represents straight-chain or branched alkyl with 1 to 6 carbon atoms, or represents aryl which has 6 to 10 carbon atoms and is optionally monosubstituted or polysubstituted by identical or different substituents, or represents a radical

possible substituents on the aryl being those mentioned for R⁴,

X³ represents oxygen or sulphur and

R⁷ represents hydrogen, or represents in each case straight-chain or branched alkyl, alkoxy, alkylamino or dialkylamino with in each case 1 to 8 carbon atoms in the individual alkyl parts.

Particularly preferred 5-acylamino-pyrazole derivatives of the formula (I) are those in which R¹ represents hydrogen, nitro, chlorine or bromine, R² represents hydrogen, or represents straight-chain or branched alkyl with 1 to 8 carbon atoms, or represents in each case straight-chain or branched alkenyl or alkinyl with in each case 3 to 6 carbon atoms, or represents cycloalkyl which has 3 to 6 carbon atoms and is optionally monosubstituted, disubstituted or trisubstituted by identical or different substituents from the group comprising methyl, ethyl and isopropyl, R³ represents hydrogen, or represents straight-chain or branched alkyl with 1 to 6 carbon atoms, or represents cycloalkyl which has 3 to 6 carbon atoms and is optionally monosubstituted, disubstituted or trisubstituted by identical or different substituents from the group comprising methyl, ethyl and isopropyl, or represents phenyl which is optionally mono-, di-, tri-, tetra- or pentasubstituted by identical or different substituents, possible substituents on the phenyl being: fluorine, chlorine, bromine, iodine, cyano, nitro, methyl, ethyl, n- or i-propyl, n-, i-, s- or t-butyl, methoxy and ethoxy, Ar represents phenyl which is optionally mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents, possible substituents on the phenyl and pyridyl in each case being: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical $-S(O)_m-R^8$, wherein R⁸ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl and m represents the number 0, 1 or 2, X¹ represents oxygen or sulphur, A represents a bridge member of the formula $-CH_2-$; $-CH_2-CH_2-$; $-CH-$; $-CCl_2-CH_2-$;
                              |
                              $CH_3$ -continued $-CHCl-CH_2-$, $-CH-CH_2-$; $-CH_2-CH_2-CH_2-$;
                |
                $CH_3$ $CH_3$
                                    |
$-CH_2-CH_2-CH_2-CH_2-$  $-C-CH_2-$; $-CH-CH_2-$;
                                    |         |
                                    $CH_3$    $Br$ $-CBr_2-CH_2-$; $-C(CH_3)_2-$; $-CH-CH-$;
                                |   |
                                $CH_3$ $CH_3$ $\begin{array}{c} H \\ | \\ -C- \\ | \\ \text{Ph} \end{array}$ or $\begin{array}{c} H \\ | \\ -C-CH_2-, \\ | \\ \text{Ph} \end{array}$ n represents the number 0 or 1 and X² represents oxygen, or represents a radical $=N-O-R^4$, or represents a radical $=N-N\begin{array}{c} R^5 \\ \\ R^6 \end{array}$ wherein R⁴ represents hydrogen, or represents straight-chain or branched alkyl with 1 to 6 carbon atoms, or represents in each case straight-chain or branched alkenyl or alkinyl with in each case 3 to 6 carbon atoms, or represents in each case straight-chain or branched halogenoalkyl with 1 to 6 carbon atoms or halogenoalkenyl with 3 to 6 carbon atoms and in each case 1 to 5 identical or different halogen atoms (in particular fluorine, chlorine or bromine), or represents in each case straight-chain or branched alkoxyalkyl or alkylthioalkyl with in each case 1 to 3 carbon atoms in the individual alkyl parts, or represents benzyl, phenethyl or phenyl, in each case mono-, di-, tri-, tetra- or pentasubstituted by identical or different substituents in the phenyl part, possible substituents on the phenyl in each case being: fluorine, chlorine, bromine, iodine, cyano, nitro, methyl, ethyl, n- or i-propyl, n-, i-, s- or t-butyl, methoxy and ethoxy, R⁵ represents hydrogen, or represents straight-chain or branched alkyl with 1 to 4 carbon atoms and R⁶ represents hydrogen, or represents straight-chain or branched alkyl with 1 to 4 carbon atoms, or represents phenyl which is optionally mono-, di-, tri-, tetra- or pentasubstituted by identical or different substituents, or represents a radical $-C-R^7,$
$\|$
$X^3$ possible substituents on the phenyl being those mentioned for R⁴, X³ represents oxygen or sulphur and R⁷ represents hydrogen, or represents straight-chain or branched alkyl with 1 to 6 carbon atoms, or represents in each case straight-chain or branched alkoxy, alkylamino or dialkylamino with in each case 1 to 4 carbon atoms in the individual alkyl parts.

Especially preferred 5-acylamino-pyrazole derivatives of the formula (I) are those in which $R^1$ represents hydrogen or nitro, $R^2$ represents hydrogen, methyl, ethyl, allyl, propargyl or cyclohexyl, $R^3$ represents hydrogen, methyl, ethyl, n- or i-propyl, n-, i-, s- or t-butyl, represents cyclopropyl, cyclobutyl, cyclopentyl, cyclohexyl, methylcyclopropyl or dimethylcyclopropyl, or represents phenyl which is optionally mono-, di-, tri-, tetra- or pentasubstituted by identical or different substituents, possible substituents on the phenyl being: cyano, nitro, fluorine, chlorine, bromine, methyl, ethyl, n- or i-propyl, n-, i-, s- or t-butyl, methoxy and ethoxy, Ar represents phenyl which is optionally mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents, possible substituents on the phenyl and pyridyl in each case being: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical $-S(O)_m-R^8$, wherein $R^8$ represents amino, methylamino, ethylamino, dimethylamino, diethylamino, fluorodichloromethyl, difluoromethyl, tetrafluoroethyl, trifluorochloroethyl, trifluoromethyl, methyl or ethyl and m represents the number 0, 1 or 2, and $X^1$ represents oxygen or sulphur, A represents a bridge member of the formula

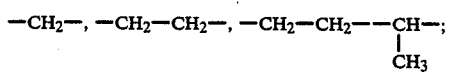

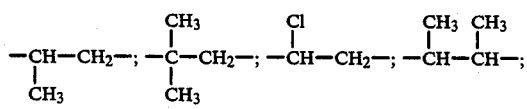

-continued

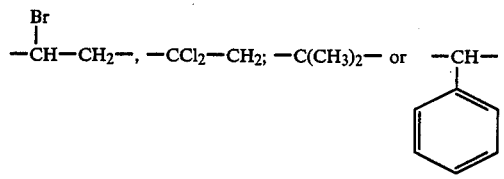

n represents the number 0 or 1 and $X^2$ represents oxygen, or represents a radical $=N-OR^4$, or represents a radical

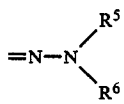

wherein $R^4$ represents hydrogen, methyl, ethyl, n- or i-propyl or n-, i-, s- or t-butyl, or represents allyl, butenyl or pentenyl, or represents propargyl, butinyl, chloroethyl, trifluoroethyl, bromoethyl, chloroallyl, bromoallyl, dichloropropenyl, chlorobutenyl, methoxymethyl, methoxyethyl, ethoxymethyl, ethoxyethyl, methylthiomethyl, methylthioethyl, ethylthiomethyl or ethylthioethyl, or represents benzyl, phenethyl or phenyl, in each case mono-, di-, tri-, tetra-or pentasubstituted by identical or different substituents in the phenyl part, possible substituents on the phenyl in each case being: fluorine, chlorine, bromine, cyano, nitro, methyl, ethyl, n- or i-propyl, n-, i-, s- or t-butyl, methoxy and ethoxy, $R^5$ represents hydrogen, methyl, ethyl, n- or i-propyl or n-, i, s- or t-butyl and $R^6$ represents hydrogen, methyl, ethyl, n- or i-propyl or n-, i-, s- or t-butyl, or represents phenyl which is optionally mono-, di-, tri-, tetra- or pentasubstituted by identical or different substituents, or represents a radical

possible substituents on the phenyl being those mentioned for $R^4$, $X^3$ represents oxygen or sulphur and $R^7$ represents hydrogen, methyl, ethyl, n- or i-propyl, n-, i-, s- or t-butyl, methoxy, ethoxy, n- or i-propoxy, n-, i-, s- or t-butoxy, methylamino, ethylamino, dimethylamino, diethylamino, propylamino or dipropylamino.

The following 5-acylamino-pyrazole derivatives of the general formula (I) may be mentioned specifically, in addition to the compounds mentioned in the preparation examples:

TABLE 1

(I) Structure: Pyrazole ring with N-Ar, R¹ at 4-position, N(R²)–C(=X¹)–(A)ₙ–C(=X²)–R³ substituent at 5-position.

| R¹ | R² | X¹ | n | A | =X²<br>–C–R³ | Ar |
|---|---|---|---|---|---|---|
| H | H | O | 0 | — | =N–OCH₃, –C–CH₃ | 2,3,5-trichloro-4-CF₃-phenyl |
| H | H | O | 0 | — | =N–OCH₃, –C–C₆H₅ | 2,3,5-trichloro-4-CF₃-phenyl |
| H | H | O | 0 | — | =N–OCH₃, –C–H | 2,3,5-trichloro-4-CF₃-phenyl |
| H | H | O | 0 | — | =N–N(CH₃)₂, –C–H | 2,3,5-trichloro-4-CF₃-phenyl |
| NO₂ | H | O | 0 | — | =N–OC₂H₅, –C–H | 2,3,5-trichloro-4-CF₃-phenyl |
| NO₂ | H | O | 0 | — | =N–NH–CH₃, –C–CH₃ | 2,3,5-trichloro-4-CF₃-phenyl |
| NO₂ | H | O | 0 | — | =N–NH–C(=O)–NH–CH₃, –C–CH₃ | 2,3,5-trichloro-4-CF₃-phenyl |

TABLE 1-continued

Structure (I):

Pyrazole core with N-Ar, substituents $R^1$, $R^2$, and $-C(=X^1)-(A)_n-C(=X^2)-R^3$ group.

| $R^1$ | $R^2$ | $X^1$ | n | A | $\overset{X^2}{-C-R^3}$ | Ar |
|---|---|---|---|---|---|---|
| $NO_2$ | H | O | 0 | — | $-C(=N-NH_2)-C_6H_5$ | 2,3,6-trichloro-4-$CF_3$-phenyl |
| $NO_2$ | H | O | 0 | — | $-C(=N-OC_2H_5)-H$ | 2,3,5,6-tetrafluoro-4-$CF_3$-phenyl |
| $NO_2$ | H | O | 0 | — | $-C(=N-OCH_3)-C_6H_5$ | 2,3,5,6-tetrafluoro-4-$CF_3$-phenyl |
| $NO_2$ | H | O | 0 | — | $-C(=N-OCH_3)-CH_3$ | 2,3,5,6-tetrafluoro-4-$CF_3$-phenyl |
| $NO_2$ | H | O | 0 | — | $-C(=N-OC_2H_5)-C_2H_5$ | 2,3,6-trichloro-4-$CF_3$-phenyl |
| $NO_2$ | H | O | 0 | — | $-C(=O)-CH_3$ | 2,3,6-trichloro-4-$CF_3$-phenyl |
| $NO_2$ | H | O | 0 | — | $-C(=O)-C_2H_5$ | 2-Br-6-Cl-4-$CF_3$-phenyl |

TABLE 1-continued $$\text{(I)}$$

Structure: Pyrazole with R¹ at 4-position, N-R² and N-Ar, with C(=X¹)-(A)ₙ-C(=X²)-R³ substituent on N-R² nitrogen.

| R¹ | R² | X¹ | n | A | $-\overset{X^2}{\underset{\|}{C}}-R^3$ | Ar |
|---|---|---|---|---|---|---|
| NO₂ | H | O | 0 | — | $-\overset{O}{\underset{\|}{C}}-C_6H_5$ | 2-Br, 6-Cl, 4-CF₃ phenyl |
| NO₂ | H | O | 0 | — | $-\overset{O}{\underset{\|}{C}}-$(4-Cl-C₆H₄) | 2-Br, 6-Cl, 4-CF₃ phenyl |
| NO₂ | H | O | 0 | — | $-\overset{O}{\underset{\|}{C}}-$(2,4-Cl₂-C₆H₃) | 2-Br, 6-Cl, 4-CF₃ phenyl |
| NO₂ | H | O | 0 | — | $-\overset{N-OCH_3}{\underset{\|}{C}}-C_6H_5$ | 2-Br, 4-CF₃ phenyl |
| NO₂ | H | O | 0 | — | $-\overset{N-OCH_3}{\underset{\|}{C}}-H$ | 2-Br, 4-CF₃ phenyl |
| NO₂ | H | O | 0 | — | $-\overset{N-OCH_3}{\underset{\|}{C}}-CH_3$ | 2-Br, 4-CF₃ phenyl |
| NO₂ | H | O | 0 | — | $-\overset{O}{\underset{\|}{C}}-H$ | 2-Cl, 4-CF₃ phenyl |
| NO₂ | H | O | 0 | — | $-\overset{N-N(CH_3)_2}{\underset{\|}{C}}-H$ | 2-Cl, 4-CF₃ phenyl |
| NO₂ | H | O | 0 | — | $-\overset{O}{\underset{\|}{C}}-CH_3$ | 2-Cl, 4-CF₃ phenyl |

TABLE 1-continued $$\text{(I)}$$

Structure: Pyrazole with R¹ at 4-position, N-R² and N-Ar substituents; N-R² nitrogen bears –C(=X¹)–(A)ₙ–C(=X²)–R³

| R¹ | R² | X¹ | n | A | $-\overset{X^2}{\underset{\|}{C}}-R^3$ | Ar |
|---|---|---|---|---|---|---|
| NO₂ | H | O | 0 | — | –C(=O)–CH₃ | 2,6-dichloro-3-fluoro-4-(trifluoromethyl)phenyl |
| NO₂ | H | O | 0 | — | –C(=N–OCH₃)–H | 2,6-dichloro-3-fluoro-4-(trifluoromethyl)phenyl |
| NO₂ | H | O | 0 | — | –C(=N–OCH₃)–CH₃ | 2,6-dichloro-3-fluoro-4-(trifluoromethyl)phenyl |
| NO₂ | H | O | 0 | — | –C(=O)–H | 2,6-dichloro-3,5-difluoro-4-chlorophenyl |
| NO₂ | H | O | 0 | — | –C(=N–OCH₃)–H | 2,6-dichloro-3,5-difluoro-4-chlorophenyl |
| NO₂ | H | O | 0 | — | –C(=N–OCH₃)–H | 2-fluoro-6-chloro-4-(trifluoromethyl)phenyl |
| NO₂ | H | O | 0 | — | –C(=N–OCH₃)–H | 2-fluoro-6-chloro-4-(trifluoromethyl)phenyl |

TABLE 1-continued

Structure (I):

Pyrazole ring with N-N, where one N bears Ar, the adjacent C bears $R^1$, and the other ring C bears $N(R^2)$—$\underset{\parallel}{C}$—$(A)_n$—$\underset{\parallel}{C}$—$R^3$ with $X^1$ and $X^2$ as the =X substituents on the two carbons.

| $R^1$ | $R^2$ | $X^1$ | n | A | $-\underset{\parallel}{\overset{X^2}{C}}-R^3$ | Ar |
|---|---|---|---|---|---|---|
| $NO_2$ | H | O | 1 | $-CH_2-$ | $-\underset{\parallel}{\overset{N-OCH_3}{C}}-H$ | 2,3,5-trichloro-4-CF$_3$-phenyl |
| $NO_2$ | H | O | 1 | $-\underset{\mid}{\overset{CH_3}{CH}}-$ | $-\underset{\parallel}{\overset{O}{C}}-H$ | 2,3,5-trichloro-4-CF$_3$-phenyl |
| $NO_2$ | H | O | 1 | $-CH_2-$ | $-\underset{\parallel}{\overset{N-OC_2H_5}{C}}-H$ | 2,5-dichloro-3-fluoro-4-CF$_3$-phenyl |
| $NO_2$ | H | O | 1 | $-\underset{\mid}{\overset{CH_3}{CH}}-$ | $-\underset{\parallel}{\overset{N-OCH_3}{C}}-C_2H_5$ | 2,5-dichloro-3-fluoro-4-CF$_3$-phenyl |
| $NO_2$ | H | O | 1 | $-CH_2-$ | $-\underset{\parallel}{\overset{N-OH}{C}}-CH_3$ | 2,3,5,6-tetrafluoro-4-CF$_3$-phenyl |
| $NO_2$ | H | O | 1 | $-\underset{\mid}{\overset{CH_3}{CH}}-$ | $-\underset{\parallel}{\overset{N-OCH_3}{C}}-H$ | 2,3,5,6-tetrafluoro-4-CF$_3$-phenyl |
| $NO_2$ | H | O | 1 | $-CH_2-$ | $-\underset{\parallel}{\overset{N-OH}{C}}-C_6H_5$ | 2,5-dichloro-4-SCF$_3$-phenyl |

TABLE 1-continued

Structure (I):

Pyrazole with R¹ at 4-position, N-Ar at 1-position, and at 5-position: N(R²)–C(=X¹)–(A)ₙ–C(=X²)–R³

| R¹ | R² | X¹ | n | A | $-\overset{X^2}{\underset{|}{C}}-R^3$ | Ar |
|---|---|---|---|---|---|---|
| NO₂ | H | O | 1 | —CH₂— | —C(=O)—H | 2,6-dichloro-4-(SO₂CF₃)phenyl |
| NO₂ | H | O | 1 | —CH₂— | —C(=O)—CH₃ | 2-chloro-4-(OCF₃)phenyl |
| NO₂ | H | O | 1 | —CH₂— | —C(=O)—C₂H₅ | 2,6-dichloro-3,5-difluoro-4-(CF₃)phenyl |
| NO₂ | H | O | 1 | —CH₂— | —C(=N—NH₂)—CH₃ | 2,3,6-trichloro-4-(CF₃)phenyl |
| NO₂ | H | O | 1 | —CH(CH₃)— | —C(=N—N(CH₃)₂)—CH₃ | 2,3,6-trichloro-4-(CF₃)phenyl |
| NO₂ | H | O | 1 | —C(CH₃)₂— | —C(=N—N(CH₃)₂)—H | 2,3,6-trichloro-4-(CF₃)phenyl |
| NO₂ | H | O | 1 | —CH₂— | —C(=N—NH—C(=S)—N(CH₃)₂)—H | 2,3,6-trichloro-4-(CF₃)phenyl |
| NO₂ | H | O | 1 | —CH(CH₃)— | —C(=N—O—CH(CH₃)₂)—H | 2,3,6-trichloro-4-(CF₃)phenyl |

TABLE 1-continued $$\text{(I)}$$

Structure: pyrazole with R¹ at 4-position, N-Ar at N1, N-R² at 5-position with C(=X¹)-(A)ₙ-C(=X²)-R³ substituent.

| R¹ | R² | X¹ | n | A | $-\underset{\underset{X^2}{\|}}{C}-R^3$ | Ar |
|---|---|---|---|---|---|---|
| NO₂ | H | O | 1 | —CH₂— | $-\underset{\underset{O}{\|}}{C}-CH(CH_3)_2$ | 2,3,5,6-tetrafluoro-4-CF₃-phenyl |
| NO₂ | H | O | 1 | —CH₂— | $-\underset{\underset{O}{\|}}{C}-C_2H_5$ | 2,3,5,6-tetrafluoro-4-CF₃-phenyl |
| NO₂ | H | O | 1 | —CH₂— | $-\underset{\underset{N-O-CH(CH_3)_2}{\|}}{C}-CH_3$ | 2,3,5,6-tetrafluoro-4-CF₃-phenyl |
| NO₂ | H | O | 1 | $-\underset{\underset{CH_3}{\|}}{CH}-$ | $-\underset{\underset{N-OH}{\|}}{C}-CH_3$ | 2,3,5,6-tetrafluoro-4-CF₃-phenyl |
| NO₂ | H | O | 1 | —CH₂— | $-\underset{\underset{N-OH}{\|}}{C}-CH_3$ | 2,3-dichloro-6-fluoro-4-CF₃-phenyl (Cl,F,Cl,CF₃) |
| NO₂ | H | O | 1 | $-\underset{\underset{CH_3}{\|}}{CH}-$ | $-\underset{\underset{O}{\|}}{C}-C_6H_5$ | 2,3-dichloro-6-fluoro-4-CF₃-phenyl |
| NO₂ | H | O | 1 | —CH₂CH₂— | $-\underset{\underset{O}{\|}}{C}-C_6H_5$ | 2,6-dichloro-4-CF₃-phenyl |

TABLE 1-continued $$\text{(I)}$$

Structure (I): pyrazole ring with N-Ar, substituent $R^1$ at 4-position, and N($R^2$)-C(=$X^1$)-(A)$_n$-C(=$X^2$)-$R^3$ at 5-position.

| $R^1$ | $R^2$ | $X^1$ | n | A | $-\overset{X^2}{\underset{\|}{C}}-R^3$ | Ar |
|---|---|---|---|---|---|---|
| $NO_2$ | H | O | 1 | $-CH_2CH_2-$ | $-C(=N-OC_2H_5)-H$ | 2,6-dichloro-4-(trifluoromethyl)phenyl |
| $NO_2$ | H | O | 1 | $-CH(CH_3)-CH(CH_3)-$ | $-C(=N-OCH_3)-H$ | 2,6-dichloro-4-(trifluoromethyl)phenyl |
| $NO_2$ | H | O | 1 | $-CH(CH_3)-CH(CH_3)-$ | $-C(=N-OCH_3)-CH_3$ | 2,6-dichloro-4-(trifluoromethyl)phenyl |
| $NO_2$ | H | O | 1 | $-CH(CH_3)-CH(CH_3)-$ | $-C(=O)-CH_3$ | 2,6-dichloro-4-(trifluoromethyl)phenyl |
| $NO_2$ | H | O | 1 | $-CH_2CH_2-$ | $-C(=O)-H$ | 2,3,5,6-tetrachloro-4-(trifluoromethyl)phenyl |
| $NO_2$ | H | O | 1 | $-CH_2CH_2-$ | $-C(=O)-CH_3$ | 2,3,5,6-tetrachloro-4-(trifluoromethyl)phenyl |
| $NO_2$ | H | O | 1 | $-CH_2CH_2-$ | $-C(=N-OCH_3)-H$ | 2,3,5,6-tetrachloro-4-(trifluoromethyl)phenyl |

TABLE 1-continued

Structure (I):

Pyrazole ring with R¹ at 4-position, N-Ar at 1-position, and at 5-position N(R²)-C(=X¹)-(A)ₙ-C(=X²)-R³

| R¹ | R² | X¹ | n | A | =X²<br>−C−R³ | Ar |
|---|---|---|---|---|---|---|
| NO₂ | H | O | 1 | −CH₂CH₂− | =N−OC₂H₅<br>−C−H | 2,3,5,6-tetrachloro-4-(CF₃)phenyl |
| NO₂ | H | O | 1 | −CH₂− | =O<br>−C−CH₃ | 2,3,5,6-tetrafluoro-4-(CF₃)phenyl |
| NO₂ | H | O | 1 | −CH₂− | =O<br>−C−(4-Cl-C₆H₄) | 2,3,5,6-tetrafluoro-4-(CF₃)phenyl |
| NO₂ | H | O | 1 | −CH₂− | =N−O−CH(CH₃)₂<br>−C−H | 2,3,5,6-tetrafluoro-4-(CF₃)phenyl |
| NO₂ | H | O | 0 | — | =N−NH₂<br>−C−CH₃ | 2,6-dichloro-4-(CF₃)phenyl |
| NO₂ | H | O | 0 | — | =N−N(CH₃)₂<br>−C−H | 2,6-dichloro-4-(CF₃)phenyl |
| NO₂ | H | O | 1 | −CH₂− | =N−N(CH₃)₂<br>−C−CH₃ | 2,6-dichloro-4-(CF₃)phenyl |

TABLE 1-continued

Structure (I):

Pyrazole with N-Ar, N-C(=X¹)-(A)ₙ-C(=X²)-R³ substituent, R¹ at 4-position, R² on N.

| R¹ | R² | X¹ | n | A | $-\underset{\underset{X^2}{\|}}{C}-R^3$ | Ar |
|---|---|---|---|---|---|---|
| NO₂ | H | O | 1 | —CH₂— | $-\underset{\underset{O}{\|}}{C}-C_2H_5$ (X²=O) | 2,6-diCl-4-CF₃-phenyl |
| NO₂ | H | O | 1 | —CH(CH₃)— | $-C(=N-OH)-C_2H_5$ | 2,6-diCl-4-CF₃-phenyl |
| NO₂ | H | O | 1 | —CH₂CH₂— | $-C(=N-N(CH_3)_2)-C_2H_5$ | 2,6-diCl-4-CF₃-phenyl |
| NO₂ | H | O | 1 | —CH₂CH₂— | $-C(=O)-CH(CH_3)_2$ | 2,6-diCl-4-CF₃-phenyl |
| NO₂ | H | O | 1 | —CH(CH₃)CH(CH₃)— | $-C(=O)-H$ | 2,6-diCl-4-CF₃-phenyl |
| NO₂ | H | O | 1 | —CH₂CH₂— | $-C(=N-N(CH_3)_2)-CH_3$ | 2,3,5-triCl-4-CF₃-phenyl |
| NO₂ | H | O | 1 | —CH₂CH₂— | $-C(=O)-CH(CH_3)_2$ | 2,3,5-triCl-4-CF₃-phenyl |

TABLE 1-continued $$\underset{\underset{\underset{X^1}{\parallel}}{\overset{R^2}{\underset{|}{N}}-\overset{\overset{X^2}{\parallel}}{C}-(A)_n-\overset{\overset{X^2}{\parallel}}{C}-R^3}}{\overset{R^1}{\underset{N-N}{\underset{|}{\underset{Ar}{}}}}}$$ (I)

| $R^1$ | $R^2$ | $X^1$ | n | A | $-\overset{\overset{X^2}{\parallel}}{C}-R^3$ | Ar |
|---|---|---|---|---|---|---|
| $NO_2$ | H | O | 1 | $-CH_2-$ | $-\overset{\overset{O}{\parallel}}{C}-C_2H_5$ | 2,3,5-Cl$_3$-4-CF$_3$-phenyl |
| $NO_2$ | H | O | 1 | $-\overset{\overset{CH_3}{\vert}}{CH}-$ | $-\overset{\overset{N-NH-\overset{\overset{S}{\parallel}}{C}-N(CH_3)_2}{\parallel}}{C}-H$ | 2,3,5-Cl$_3$-4-CF$_3$-phenyl |
| $NO_2$ | H | O | 1 | $-CH_2-$ | $-\overset{\overset{N-NH_2}{\parallel}}{C}-H$ | 2,3,5-Cl$_3$-4-CF$_3$-phenyl |
| $NO_2$ | $CH_3$ | O | 0 | — | $-\overset{\overset{N-NH_2}{\parallel}}{C}-CH_3$ | 2,3,5-Cl$_3$-4-CF$_3$-phenyl |
| $NO_2$ | $CH_3$ | O | 0 | — | $-\overset{\overset{O}{\parallel}}{C}-H$ | 2,3,5-Cl$_3$-4-CF$_3$-phenyl |
| $NO_2$ | $CH_3$ | O | 0 | — | $-\overset{\overset{N-OCH_3}{\parallel}}{C}-CH_3$ | 2,3,5-Cl$_3$-4-CF$_3$-phenyl |
| $NO_2$ | $CH_3$ | O | 1 | $-CH_2-$ | $-\overset{\overset{N-OC_2H_5}{\parallel}}{C}-H$ | 2,3,5-Cl$_3$-4-CF$_3$-phenyl |

If, for example, 5-amino-1-(2,4-dichlorophenyl)-pyrazole and α-methoximinophenylacetyl chloride are used as starting substances, the course of the reaction in process (a) according to the invention can be reprresented by the following equation:

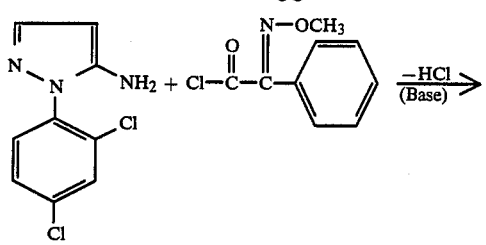

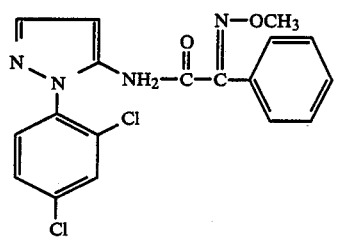

If, for example, 1-(4-chlorophenyl)-5-methoximino-acetamido-pyrazole and methyl iodide are used as starting substances, the course of the reaction in process (b) according to the invention can be represented by the following equation:

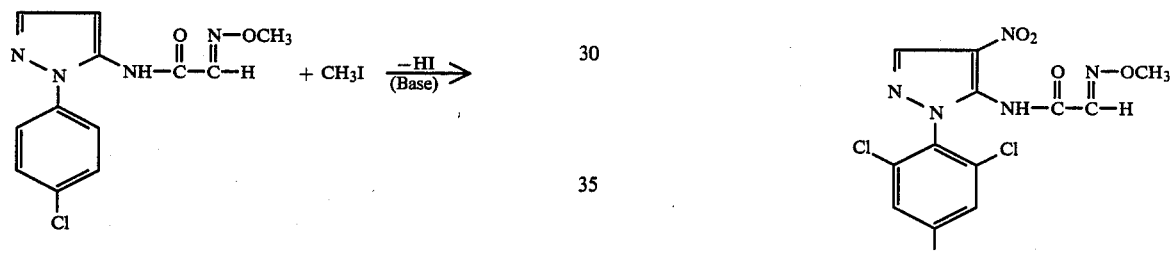

If, for example, 5-acetoacetylamino-1-(2-chloro-4-trifluoromethyl-phenyl)-4-nitro-pyrazole and N,N-dimethylhydrazine are used as starting substances, the course of the reaction in process (c) according to the invention can be represented by the following equation:

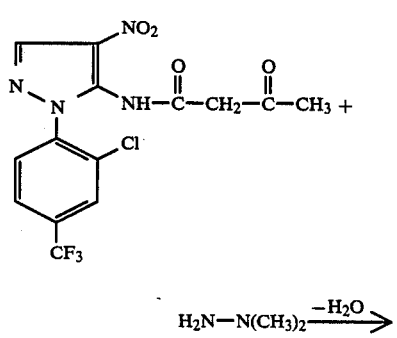

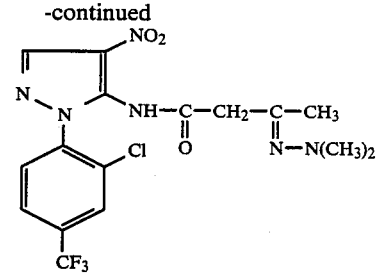

If, for example, 1-(2,4,6-trichlorophenyl)-5-methoximinoacetamido-pyrazole and nitric acid are used as starting substances, the course of the reaction in process (d) according to the invention can be represented by the following equation:

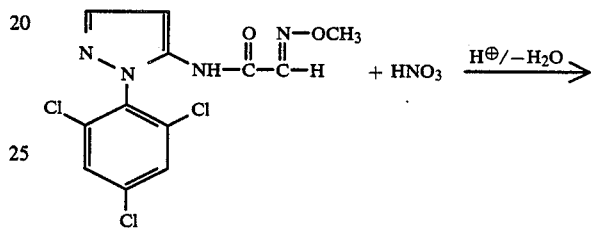

Formula (II) provides a general definition of the 5-amino-1-arylpyrazoles required as starting substances for carrying out process (a) according to the invention. In this formula (II), $R^1$ and Ar preferably represent those radicals which have already been mentioned as preferred for these substituents in connection with the description of the substances of the formula (I) according to the invention.

The 5-amino-1-aryl-pyrazoles of the formula (II) are known in some cases (for example, U.S. application Ser. No. 690,347, filed Jan. 10, 1985, now pending, and U.S. application Ser. No. 866,638, filed May 22, 1986, now pending) and are obtainable by processes analogous to known processes (for example, U.S. application Ser. No. 690,347, supra) for example by a procedure in which arylhydrazines of the formula (VII)

Ar—NH—NH₂ (VII)

in which

Ar has the abovementioned meaning, and 2-halogenoacrylonitriles of the formula (VIII)

in which

Hal represents halogen, in particular chlorine or bromine, are either initially reacted in a 1st stage, if appropriate in the presence of a diluent, such as, for example, glacial acetic acid or ethanol, and if appropriate in the presence of a reaction auxiliary, such as, for example, sodium acetate, at temperatures between $-20°$ C. and $+20$ C., to give the arylhydrazine derivatives of the formula (IX)

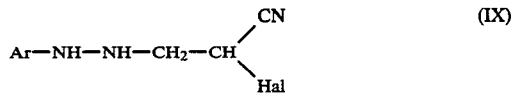

in which

Ar and Hal have the abovementioned meaning, and these are cyclized in a 2nd stage, if appropriate in the presence of a diluent, such as, for example, ethylene glycol monoethyl ether, and if appropriate in the presence of an acid catalyst, such as, for example, sulphuric acid or phosphoric acid, at temperatures between $+50°$ C. and $+150°$ C., or are cyclized directly in one reaction step without isolation of the intermediate stage of the formula (IX), if appropriate in the presence of a diluent, such as, for example, ethylene glycol monoethyl ether or ethanol, at temperatures between $+50°$ C. and $+150°$ C., and, if appropriate, the 4-unsubstituted 5-amino-1-aryl-pyrazoles thus obtainable, of the formula (IIa)

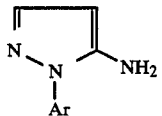

in which

Ar has the abovementioned meaning, are nitrated in a secondary reaction with a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between $-20°$ C. and $+50°$ C., or, alternatively, are halogenated with a halogenating agent, such as, for example, chlorine, sulphuryl chloride, phosphorus pentachloride, N-chlorosuccinimide, bromine, phosphorus tribromide or N-bromosuccinimide, if appropriate in the presence of a diluent, such as, for example, methylene chloride or glacial acetic acid, and if appropriate in the presence of a reaction auxiliary, such as, for example, boron trifluoride, at temperatures between $-20°$ C. and $+50°$ C.

If appropriate, it may be of advantage here for the amino group in the 5-position of the pyrazole ring to be protected with the aid of the customary protective group technique, for example by acylation, before the halogenation or nitration reaction and for the aminoprotective group to be split off again, likewise in the customary manner, for example by hydrolysis with an aqueous or alcoholic base, after the halogenation or nitration has been carried out.

The arylhydrazines of the formula (VII) are known (compare, for example, U.S. Pat. No. 4,127,575; U.S. Pat. No. 3,609,158; DE-OS (German Published Specification) No. 2,558,399; and J. Chem. Soc. C. 1971, 167–174), or they can be obtained by known processes in a simple analogous manner (compare, for example, Houben-Weyl "Methoden der organischen Chemie" ("Methods of Organic Chemistry"), Volume X/2, page 203, Thieme Verlag Stuttgart 1967; and DE-OS (German Published Specification) No. 3,402,308).

The halogenoacrylonitriles of the formula (VIII) are generally known compounds of organic chemistry.

Formula (III) provides a general definition of the acylating agents furthermore required as starting substances for carrying out process (a) according to the invention. In this formula (III), $X^1$, $X^2$, $R^3$, A and the index n preferably have those meanings which have already been mentioned as preferred for these substituents in connection with the description of the substances of the formula (I) according to the invention.

$E^1$ preferably represents halogen, in particular chlorine or bromine, or represents a radical

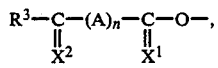

wherein $X^1$, $X^2$, $R^3$, A and the index n have the abovementioned meanings.

The acylating agents of the formula (III) are generally known compounds of organic chemistry or are obtainable by generally known processes analogously to known compounds [compare, for example: DE-OS (German Published Specification) No. 3,208,329; DE-OS (German Published Specification) No. 3,208,330; Org. Syntheses 61, 1–4 (1983), J. org. Chem. 46, 3346–3348 (1981); and J. chem. Soc. Chem. Commun. 1180–1181 (1979)].

Formula (Ia) provides a general definition of the 5-acylamino-pyrazole derivatives required as starting substances for carrying out process (b) according to the invention. In this formula (Ia), $R^1$, $R^3$, $X^1$, $X^2$, A the index n and Ar preferably have those meanings which have already been mentioned as preferred for these substituents in connection with the description of the substances of the formula (I) according to the invention.

The 5-acylamino-pyrazole derivatives of the formula (Ia) are compounds according to the invention and are obtainable with the aid of process (a), (c) or (d) according to the invention.

Formula (IV) provides a general definition of the alkylating agents furthermore required as starting substances for carrying out process (b) according to the invention. In this formula (IV), $R^{2-1}$ preferably represents straight-chain or branched alkyl with 1 to 12 carbon atoms, or represents in each case straight-chain or branched alkenyl or alkinyl with in each case 3 to 8 carbon atoms, or represents cycloalkyl which has 3 to 8 carbon atoms and is optionally monosubstituted or poly-substituted by identical or different $C_1$–$C_4$-alkyl radicals.

$R^{2-1}$ particularly preferably represents straight-chain or branched alkyl with 1 to 8 carbon atoms, or represents in each case straight-chain or branched alkenyl or alkinyl with in each case 3 to 6 carbon atoms, or represents cycloalkyl which has 3 to 6 carbon atoms and is optionally monosubstituted, disubstituted or trisubstituted by identical or different substituents from the group comprising methyl, ethyl and isopropyl.

$R^{2-1}$ particularly represents methyl, ethyl, allyl, propargyl or cyclohexyl.

$E^2$ preferably represents chlorine, bromine or iodine, or represents methoxysulphonyloxy, or represents p-toluenesulphonyloxy.

The alkylating agents of the formula (IV) are generally known compounds of organic chemistry.

Formula (Ie) provides a general definition of the 5-acylamino-pyrazoles required as starting substances for carrying out process (c) according to the invention. In this formula (Ie), $R^1$, $R^2$, $R^3$, $X^1$, A, Ar and the index n preferably have those meanings which have already been mentioned as preferred for these substituents in connection with the description of the substances of the formula (I) according to the invention.

The 5-acylamino-pyrazoles of the formula (Ie) are compounds according to the invention and are obtainable with the aid of process (a), (b) or (d) according to the invention.

Formula (V) provides a general definition of the primary amino compounds furthermore required as starting substances for carrying out process (c) according to the invention. In this formula (V), Y preferably represents a radical —$OR^4$ or a radical

wherein $R^4$, $R^5$ and $R^6$ preferably represent those radicals which have already been mentioned as preferred for these substituents in connection with the description of the substances of the formula (I) according to the invention.

The primary amino compounds of the formula (V) are generally known compounds of organic chemistry.

Formula (If) provides a general definition of the 5-acylamino-pyrazole derivatives required as starting substances for carrying out process (d) according to the invention. In this formula (If), $R^2$, $R^3$, $X^1$, $X^2$, A, Ar and the index n preferably have those meanings which have already been mentioned as preferred for these substituents in connection with the description of the substances of the formula (I) according to the invention.

The 5-acylamino-pyrazole derivatives of the formula (If) are compounds according to the invention and are obtainable with the aid of process (a), (b) or (c) according to the invention.

Formula (VI) provides a general definition of the halogenating or nitrating agents furthermore required as starting substances for carrying out process (d) according to the invention. In this formula (VI), $R^{1-1}$ preferably represents chlorine, bromine or nitro. $E^3$ preferably represents a customary leaving group, such as, for example, halogen and phosphorus- or sulphur-containing halogenated leaving groups. Examples of suitable halogenating and nitrating agents are nitric acid, nitrating acid, sulphuryl chloride, phosphorus oxychloride, phosphorus oxybromide, phosphorus tribromide and similar generally customary halogenating and nitrating agents.

The halogenating and nitrating agents of the formula (VI) are generally known compounds.

Possible diluents for carrying out process (a) according to the invention are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as diemethylformamide, dimethylacetamide, N-methylformanilide, N-methylpyrrolidone or hexamethylphosphoric acid triamide, esters, such as ethyl acetate, or sulphoxides, such as dimethylsulphoxide.

If appropriate, process (a) according to the invention is carried out in the presence of a suitable acid-binding agent.

Possible acid-binding agents are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

If appropriate, process (a) according to the invention can also be carried out in the presence of a suitable acylating catalyst. Acylating catalysts which are used are, preferably, proton acids, such as sulphuric acid, hydrochloric acid, phosphoric acid or trifluoroacetic acid, or Lewis acids, such as aluminum trichloride, boron trifluoride or iron trichloride.

The reaction temperatures can be varied within a substantial range in carrying out process (a) according to the invention. The reaction is in general carried out at temperatures between −20° C. and +150° C., preferably at temperatures between 0° C. and 100° C.

For carrying out process (a) according to the invention, in general 1.0 to 15.0 mols, preferably 1.0 to 5.0 mols, of acylating agent of the formula (III), if appropriate 1.0 to 3.0 mols, preferably 1.0 to 2.0 mols, of acid-binding agent or if appropriate 0.1 to 3.0 mols, preferably 0.1 to 2.0 mols, of acylating catalyst are employed per mol of 5-amino-1-aryl-pyrazole of the formula (II). It is also possible for the acylating agents of the formula (III) to be prepared by generally known processes in a prior reaction and to be further reacted in process (a) according to the invention directly from the reaction mixture in a "one-pot process" (compare the preparation examples). The reaction is carried out and the reaction products of the formula (Ia) are worked up and isolated by customary known methods.

Possible diluents for carrying out process (b) according to the invention are likewise inert organic solvents. The organic solvents mentioned for process (a) are preferably used.

If appropriate, process (b) according to the invention can also be carried out in a two-phase system, such as, for example, water/toluene or water/methylene chloride, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyldimethylammonium methyl sulphate, dimethyl-$C_{12}/C_{14}$-alkyl-benzylammonium chloride, tetrabutylammonium hydroxide, 15-crown-5, 18-crown-6, triethylbenzylammonium chloride and trimethylbenzylammonium chloride.

Possible acid-binding agents for carrying out preparation process (b) are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out process (b) according to the invention. The reaction is in general carried out at temperatures between $-20°$ C. and $+150°$ C., preferably at temperatures between $0°$ C. and $+100°$ C.

For carrying out process (b) according to the invention, in general 1.0 to 20.0 mols, preferably 1.0 to 15.0 mols, of alkylating agent of the formula (IV) and if appropriate 1.0 to 3.0 mols, preferably 1.0 to 2.0 mols, of acid-binding agent and 0.01 to 1.0 mol of phase transfer catalyst are employed per mol of 5-acylamino-pyrazole derivatives of the formula (Ia). The reaction is carried out and the reaction products of the formula (Ib) are worked up and isolated in the generally customary manner.

Possible diluents for carrying out process (c) according to the invention are inert organic solvents or aqueous systems. The organic solvents mentioned for process (a) are preferably used. Other solvents preferred as diluents are polar organic solvents, such as methanol, ethanol, n-propanol, i-propanol, n-butanol, i-butanol, t-butanol, ethylene glycol, diethylene glycol, ethylene glycol monomethyl ether or monoethyl ether, diethylene glycol monoethyl ether or monoethyl ether, mixtures thereof with water and also pure water.

If appropriate, process (c) according to the invention can be carried out in the presence of a suitable reaction auxiliary. Reaction auxiliaries which are employed are usually inorganic or organic acids. p-Toluenesulphonic acid is the particularly preferred reaction auxiliary.

The reaction temperatures can be varied within a substantial range in carrying out process (c) according to the invention. The reaction is in general carried out at temperatures between $-20°$ C. and $100°$ C., preferably at temperatures between $20°$ C. and $80°$ C.

For carrying out process (c) according to the invention, in general 1.0 to 10.0 mols, preferably 1.0 to 5.0 mols, of primary amino compound of the formula (V) and if appropriate 0.01 mol to 1.0 mol of reaction auxiliary are employed per mol of 5-acylamino-pyrazole derivative of the formula (Ie). It is also possible to use the primary amino compounds of the formula (V) in the form of their acid addition salts, such as, for example, their hydrohalides. If appropriate, it can be of advantage to add an equimolar amount or less of a suitable auxiliary base, such as, for example, triethylamine or pyridine. The reaction is carried out and the reaction products of the formula (Ic) are worked up and isolated by generally known processes.

Possible diluents for carrying out preparation process (d) are all the solvents which can usually be employed for such electrophilic substitution reactions. The acids or mixtures suitable as reagents, such as, for example, nitric acid, nitrating acid, sulphuryl chloride or nitrating acid, are preferably simultaneously used as the diluent. If appropriate, inert organic solvents, such as, for example, glacial acetic acid or chlorinated hydrocarbons, such as methylene chloride, chloroform or carbon tetrachloride, are also suitable as diluents.

Possible catalysts or reaction auxiliaries for carrying out preparation process (d) are likewise the catalysts customary for such reactions; acid catalysts, such as, for example, sulphuric acid, iron-III chloride or other Lewis acids or acetic anhydride, are preferably used.

The reaction temperatures can be varied within a substantial range in carrying out preparation process (d). The reaction is in general carried out between $-50°$ C. and $+200°$ C., preferably between $-20°$ C. and $+150°$ C.

For carrying out preparation process (d), in general 1.0 to 10.0 mols, preferably 1.0 to 5.0 mols, of halogenating or nitrating agent of the formula (VI) and if appropriate 0.1 and 10 mols of catalyst or reaction auxiliary are employed per mol of 5-acylamino-pyrazole derivative of the formula (If). The reaction is carried out and the reaction products of the formula (Id) are worked up and isolated in the generally customary manner.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used with particularly good success for selectively combating monocotyledon and dicotyledon weeds, in monocotyledon and dicotyledon crops, such as, for example, wheat or cotton.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, wettable powders, suspensions, powders, dusting agents, foams, pastes, soluble powders, granules, suspension-emulsion concentrates, natural and synthetic materials impregnated with active compound, aerosols, very fine capsules in polymeric substances and in coating compositions for use on seed, as well as ULV formulations.

These formulations are produced in known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide.

As solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxy-ethylene-fatty acid esters, polyoxyethylene-fatty alcohol ethers, for example alkylaryl polyglycol ethers, alkylsulphonates, alkylsulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4-(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soya bean. - Mixtures with 2-chloro-N-{[(4-methoxy-6-methyl-1,3,5-triazin-2-yl)-amino]-carbonyl}-benzenesulphonamide; N,N-dimethyl-N'-(3-chloro-4-methylphenyl)-urea; N,N- dimethyl-N'-(4-isopropylphenyl)-urea; 4-ethylamino-2-t-butylamino-6-methylthio-s-triazine; 2-chloro-4-ethylamino-6-isopropylamino-1,3,5-triazine; 2-chloro-4,6-bis(ethylamino)-1,3,5-triazine; 2-chloro-4-ethylamino-6-(3-cyanopropylamino)-1,3,5-triazine; 4-amino-6-t-butyl-3-ethylthio-1,2,4-triazin-5(4H)-one; trimethylsilylmethyl 2-[4-(3,5-dichloropyrid-2-yloxy)-phenoxy]-propionate; 2[4-(2,4-dichlorophenoxy)-phenoxy]-propionic acid or its methyl or ethyl ester; 2-{4-[(6-chloro-2-benzoxazolyl)oxy]-phenoxy}-propanoic acid or its methyl or ethyl ester; methyl 5-(2,4-dichlorophenoxy)-2-nitrobenzoate; methyl 2-[4,5-dihydro-4-methyl-4-(1-methylethyl)-5-oxo-1H-imidazol-2-yl]-4(5)-methylbenzoate; 3,5-diiodo-4-hydroxybenzonitrile; 3,5-dibromo-4-hydroxy-benzonitrile; 2,4-dichlorophenoxyacetic acid; 2,4-dichlorophenoxypropionic acid; (4-chloro-2-methylphenoxy)-propionic acid; (2-methyl-4-chlorophenoxy)-acetic acid; [(4-amino-3,5-dichloro-6-fluoro-2-pyridinyl)-oxy]-acetic acid or its 1-methylheptyl ester; 0-(6-chloro-3-phenyl-pyridazin-4-yl) S-octyl thiocarbonate and 3-isopropyl-2,1,3-benzothiadiazin-4-one 2,2-dioxide, where appropriate, are also of advantage.

Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

When used by the post-emergence method, the compounds according to the invention can be applied by themselves or in combination with emulsifiable oils, surface-active substances and other additives.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the active compounds according to the invention can likewise be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

In the treatment of parts of plants, the active compound concentrations in the use forms can be varied within a substantial range. They are in general between 1 and 0.0001% by weight, preferably between 0.5 and 0.001% by weight.

In the treatment of seed, active compound amounts of 0.001 to 50 g, preferably 0.01 to 10 g, are required per kilogram of seed.

In the treatment of the soil, active compound concentrations of 0.00001 to 0.1% by weight, preferably 0.0001 to 0.02% by weight, are required at the place of action.

The amounts applied can be varied within a substantial range. In general, 0.01 to 50 kg, preferably 0.05 to 10 kg, of active compound are used per hectare of soil surface.

As regards the time of application, the growth regulators are applied within a preferred period of time, the exact definition of which depends on the climatic and vegetative circumstances.

The preparation and use of the active compounds according to the invention can be seen from the following examples:

PREPARATION EXAMPLES

Example 1

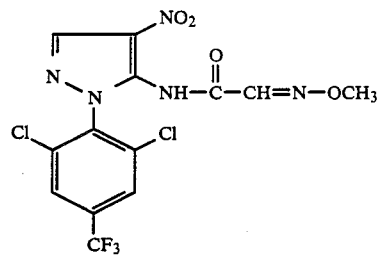

(Process d)

2.5 ml (2.7 g/0.045 mol) of acetic anhydride and then 2.5 ml (2.6 g/0.06 mol) of 98 per cent strength nitric acid are added in succession to 7.6 g (0.02 mol) of 5-methoximinoacetyl-amino-1-(2,6-dichloro-4-trifluoromethyl-phenyl)-pyrazole in 50 ml of glacial acetic acid at 10° C. to 15° C. When the addition has ended, the reaction mixture is stirred at 20° C. to 25° C. for 3 hours and then poured into water and extracted with toluene, the organic phase is washed twice with water and once with sodium bicarbonate solution, dried over sodium sulphate and concentrated in vacuo and the residue is crystallized by trituration with ligroin.

4.5 g (53% of theory) of 4-nitro-5-methoximinoacetyl-amino-1-(2,6-dichloro-4-trifluoromethylphenyl)-pyrazole of melting point 107° C.–109° C. are obtained.

Example 2

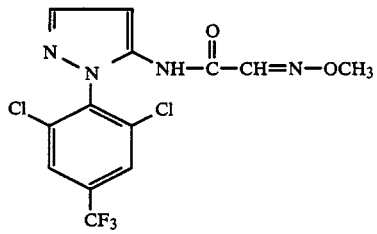

(Process a)

First 8 g (0.1 mol) of pyridine and then, dropwise at 0° C. to 5° C., 12 g (0.1 mol) of thionyl chloride are added to 10.5 g (0.1 mol) of methoximinoacetic acid (compare DE-OS (German Published Specification) No. 3,208,329) in 100 ml of acetonitrile. When the addition has ended, the mixture is stirred at 30° C. for 3 hours, 15 g (0.05 mol) of 5-amino-1-(2,6-dichloro-4-trifluoromethylphenyl)pyrazole (compare U.S. patent application Ser. No. 690,347 supra) are subsequently added and a further 4 g (0.05 mol) of pyridine are then added. Thereafter, the reaction mixture is stirred at 20° C. to 25° C. for a further 12 hours and poured into water and the crystalline precipitate is filtered off with suction and dried on clay.

15.4 g (81% of theory) of 5-methoximinoacetylamino-1-(2,6-dichloro-4-trifluoromethylphenyl)-pyrazole of melting point 158° C.–160° C. are obtained.

The following 5-acylamino-pyrazole derivatives of the general formula (I) are obtained in a corresponding manner and in accordance with the general statements on the preparation:

TABLE 2
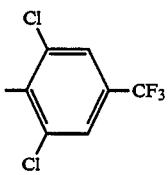
(I)
| Example | R¹ | R² | $-\overset{X^1}{\underset{\|}{C}}-(A)_n-\overset{X^2}{\underset{\|}{C}}-R^3$ | Ar | Melting point/°C |
|---|---|---|---|---|---|
| 3 | H | H | -CO-C(=N-OCH₃)-CH₃ | 2,6-di-Cl-4-CF₃-phenyl | 96-98 |
| 4 | H | H | -CO-C(=N-OCH₃)-CH₃ | 2,3,5-tri-Cl-4-CF₃-phenyl | 91 |
| 5 | NO₂ | H | -CO-C(=N-OCH₃)-CH₃ | 2,6-di-Cl-4-CF₃-phenyl | 150-152 |
| 6 | NO₂ | H | -CO-C(=N-OCH₃)-CH₃ | 2,3,5-tri-Cl-4-CF₃-phenyl | 143-146 |
| 7 | NO₂ | H | -CO-C(=N-OCH₃)-H | 2,3,5,6-tetra-F-4-CF₃-phenyl | oil |
| 8 | H | H | -CO-C(=N-OCH₃)-H | 2,3,5,6-tetra-F-4-CF₃-phenyl | 108-112 |
| 9 | H | H | -CO-CH₂-C(=N-OCH₃)-H | 2,6-di-Cl-4-CF₃-phenyl | 104-105 |

TABLE 2-continued

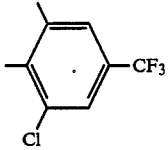
(I)

| Example | $R^1$ | $R^2$ | $-\underset{X^1}{\overset{X^1}{C}}-(A)_n-\underset{X^2}{\overset{X^2}{C}}-R^3$ | Ar | Melting point/°C. |
|---|---|---|---|---|---|
| 10 | H | H | 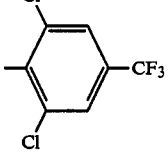 -C(=O)-CH₂-C(=O)-CH₃ | 2,6-Cl₂-4-CF₃-phenyl | 73–75 |
| 11 | NO₂ | H | -C(=O)-CH₂-C(=O)-CH₃ | 2,6-Cl₂-4-CF₃-phenyl | 64–84 |
| 12 | NO₂ | H | -C(=O)-C(=N-OCH₃)-H | 2-Cl-5-F-4-CF₃-phenyl | 88–93 |
| 13 | NO₂ | H | -C(=O)-C(=N-OCH₃)-H | 2,5-Cl₂-3-F-4-CF₃-phenyl | 113–118 |
| 14 | NO₂ | H | -C(=O)-C(=N-OCH₃)-H | 2,3,5-Cl₃-4-CF₃-phenyl | 147–152 |
| 15 | NO₂ | H | -C(=O)-C(=N-OCH₃)-phenyl | 2,6-Cl₂-4-CF₃-phenyl | 90 |
| 16 | NO₂ | H | -C(=O)-O-C(=N-OCH₃)-phenyl | 2,3,5,6-F₄-4-CF₃-phenyl | Oil |

TABLE 2-continued $$\text{(I)}$$

Structure (I): pyrazole with N-Ar, N-N, R¹ at 4-position, N(R²)–C(=X¹)–(A)ₙ–C(=X²)–R³ substituent at 5-position.

| Example | R¹ | R² | —C(=X¹)—(A)ₙ—C(=X²)—R³ | Ar | Melting point/°C. |
|---|---|---|---|---|---|
| 17 | NO₂ | H | —C(=O)—C(=N—OC₂H₅)—H | 2,6-F₂-3,5-F₂-4-CF₃-phenyl | 100–102 |
| 18 | NO₂ | H | —C(=O)—C(=N—OC₂H₅)—CH₃ | 2,3-Cl₂-5-Cl-4-CF₃-phenyl | 129–133 |
| 19 | NO₂ | H | —C(=O)—C(=N—OC₂H₅)—CH₃ | 2,6-Cl₂-4-CF₃-phenyl | 114–120 |
| 20 | NO₂ | H | —C(=O)—C(=N—OC₂H₅)—CH₃ | 2,3,5,6-F₄-4-CF₃-phenyl | 40–43 |
| 21 | NO₂ | H | —C(=O)—C(=N—OC₂H₅)—H | 2,6-Cl₂-4-CF₃-phenyl | 127–129 |
| 22 | NO₂ | H | —C(=O)—C(=N—OC₂H₅)—H | 2,3-Cl₂-5-Cl-4-CF₃-phenyl | 163–171 |
| 23 | NO₂ | H | —C(=O)—C(=N—OCH₃)—CH₃ | 2,3,5,6-F₄-4-CF₃-phenyl | 134–138 |

TABLE 2-continued

Structure (I):

Pyrazole of formula (I) with substituents R¹, R², N—R² bearing C(=X¹)—(A)ₙ—C(=X²)—R³, and N—Ar.

| Example | R¹ | R² | —C(=X¹)—(A)ₙ—C(=X²)—R³ | Ar | Melting point/°C |
|---|---|---|---|---|---|
| 24 | NO₂ | H | —C(=O)—C(=N—OCH₃)—CH₃ | 2,6-dichloro-3-fluoro-4-CF₃-phenyl (Cl, F, CF₃, Cl) | 138–140 |
| 25 | NO₂ | H | —C(=O)—C(=N—OCH₃)—H | 2-Br-5-CF₃-phenyl | Oil |
| 26 | NO₂ | H | —C(=O)—C(=N—OCH₃)—CH₃ | 2-Br-5-CF₃-phenyl | 145–149 |
| 27 | NO₂ | H | —C(=O)—C(=N—OC₂H₅)—CH₃ | 2-Br-5-CF₃-phenyl | 92–94 |
| 28 | NO₂ | H | —C(=O)—C(=O)—C₆H₅ | 2,6-dichloro-4-CF₃-phenyl | 142–150 |
| 29 | NO₂ | H | —C(=O)—C(=O)—C₆H₅ | 2,3,5,6-tetrafluoro-4-CF₃-phenyl | 129–133 |

USE EXAMPLES

The compund shown below was used as the comparison substance in the use examples which follow:

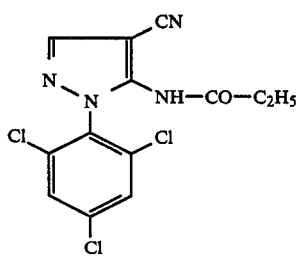

(A) 4-cyano-5-propionamido-1-(2,4,6-trichlorophenyl)-pyrazole (known from DE-OS (German Published Specification) No. 3,226,513)

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity against weeds, such as, for example, Galium, Stellaria and Portulaca and a clearly superior selectivity towards useful plants, such as, for example, in wheat, to comparison substance (A) is shown, for example, by the compounds according to Preparation Examples 1, 5, 6, 7, 17, 20, 21, 22, 23 and 24.

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in damage in comparison to the development of the untreated control. The figures denote:

0% = no action (like untreated control)
100% = total destruction

In this test, a clearly superior activity against weeds, such as, for example, Cassia, Chenopodium and Portulaca, and a clearly superior selectivity towards useful plants, such as, for example, wheat, to comparison substance (A) is shown, for example, by the compounds according to Preparation Examples 1, 5, 6, 7, 12, 13, 14, 16, 17, 18, 19, 20, 21, 22, 23, 24, 25, 26 and 27.

Example C

Defoliation and desiccation of the leaves of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings:
0 denotes no desiccation of leaves, no shedding of leaves
+ denotes slight desiccation of the leaves, slight shedding of leaves
+ + denotes severe desiccation of the leaves, severe shedding of leaves
+ + + denotes very severe desiccation of the leaves, very severe shedding of leaves.

In this test, for example, the compounds according to Preparation Examples 1, 5 and 6 show a clear activity in comparison with the untreated control.

It is understood that the specification and examples are illustrative but not limitative of the present invention and that other embodiments within the spirit and scope of the invention will suggest themselves to those skilled in the art.

We claim:

1. A 5-acylamino-pyrazole derivative

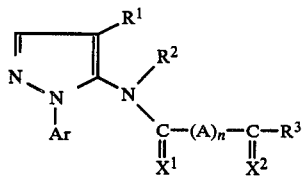

in which
$R^1$ represents hydrogen, nitro, fluorine, chlorine, bromine or iodine,
$R^2$ represents hydrogen, or represents straight-chain or branched alkyll with to 12 carbon atoms, or represents in each case straight-chain or branched alkenyl or alkinyl with in each case 3 to 8 carbon atoms, or represents cycloalkyl which has 3 to 8 carbon atoms and is optionally mono- or polysubstituted by identical or different $C_1$-$C_4$-alkyl radicals,
$R^3$ represents hydrogen, or represents straight-chain or branched alkyl with 1 to 8 carbon atoms, or represented cycloalkyl which has 3 to 8 carbon atoms and is optionally monosubstituted or polysubstituted by identical or different $C_1$-$C_4$-alkyl radicals, or represents aryl which has 6 to 10 carbon atoms and is optionally monosubstituted or polysubstituted by identical or different substituents selected from the group consisting of halogen, cyano, nitro and in each case straight-chain or branched alkyl and alkoxy with in each case 1 to 4 carbon atoms,
Ar represents 2-pyridyl, 3-pyridyl or 4-pyridyl, or phenyl, 2-pyridyl, 3-pyridyl or 4-pyridyl, in each case monosubstituted or polysubstituted by identical or different substituents selected from the group consisting of halogen, cyano, nitro, in each case straight-chain or branched alkyl, alkoxy and alkoxycarbonyl with in each case 1 to 4 carbon atoms in the alkyl part, in each case straight-chain or branched halogenoalkyl and halogenoalkoxy with in each case 1 to 4 carbon atoms and 1 to 9 identical or different halogen atoms, and a radical —S(O)m—$R^8$,
wherein
$R^8$ represents amino, or represents in each case straight-chain or branched alkyl, alkylamino, dialkylamino or halogenoalkyl with in each case 1 to 4 carbon atoms in the individual alkyl parts and, in the case of halogenoalkyl, with 1 to 9 identical or different halogen atoms and
m represents the number 0, 1 or 2,
$X^1$ represents oxygen or sulphur,
A represents a straight-chain or branched alkylene bridge which has 1 to 6 carbon atoms and is optionally monosubstituted or polysubstituted by identical or different substituents from the group consisting of phenyl, which is optionally monosubstituted or polysubstituted by identical or different halogen or $C_1$-$C_4$-alkyl radicals, and halogen, n represents the number 0 or 1 and $X^2$ represents oxygen, or represents a radical =N—O—$R^4$, or represents a radical

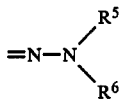

wherein $R^4$ represents hydrogen, or represents straight-chain or branched alkyl with 1 to 8 carbon atoms, or represents in each case straight-chain or branched alkenyl or alkinyl with in each case 3 to 8 carbon atoms, or represents in each case straight-chain or branched halogenoalkyl with 1 to 8 carbon atoms or halogenolkenyl with 3 to 8 carbon atoms and in each case 1 to 9 identical or different halogen atoms, or represents in each case straight-chain or branched alkoxyalkyl or alkylthioalkyl with in each case 1 to 4 carbon atoms in the individual alkyl parts, or represents aralkyl with 1 to 4 carbon atoms in the alkyl part or aryl, with in each case 6 to 10 carbon atoms in the aryl part and in each case monosubstituted or polysubstituted in the aryl part by identical or different substituents selected from the group consisting of halogen, cyano, nitro and in each case straight-chain or branched alkyl or alkoxy with in each case 1 to 4 carbon atoms, $R^5$ represents hydrogen, or represents straight-chain or branched alkyl with 1 to 6 carbon atoms and $R^6$ represents hydrogen, or represents straight-chain or branched alkyl with 1 to 6 carbon atoms, or represents aryl which has 6 to 10 carbon atoms and is optionally monosubstituted or polysubstituted by identical or different substituents, or represents a radical

possible substitutents on the aryl being those mentioned for $R^4$, $X^3$ represents oxygen or sulphur and $R^7$ represents hydrogen, or represents in each case straight-chain or branched alkyl, alkoxy, alkylamino or dialkylamino with in each case 1 to 8 carbon atoms in the individual alkyl parts.

2. A 5-acylamino-pyrazole derivative according to claim 1, in which $R^1$ represents hydrogen, nitro, chlorine or bromine, $R^2$ represents hydrogen, or represents straight-chain or branched alkyl with 1 to 8 carbon atoms, or represents in each case straight-chain or branched alkenyl or alkinyl with in each case 3 to 6 carbon atoms, or represents cycloalkyl which has 3 to 6 carbon atoms and is optionally monosubstituted, disubstituted or trisubstituted by identical or different substituents from the group consisting of methyl, ethyl and isopropyl, $R^3$ represents hydrogen, or represents straight-chain or branched alkyl with 1 to 6 carbon atoms, or represents cycloalkyl which has 3 to 6 carbon atoms and is optionally monosubstituted, disubstituted or trisubstituted by identical or different substituents from the group consisting of methyl, ethyl and isopropyl, or represents phenyl which is optionally mono-, di-, tri-, tetra- or pentasubstituted by identical or different substituents, selected from the group consisting of fluorine, chlorine, bromine, iodine, cyano, nitro, methyl, ethyl, n- or i-propyl, n-, i-, s- or t-butyl, methoxy and ethoxy, Ar represents phenyl which is mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents, possible substituents on the phenyl and pyridyl in each case being cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)m—$R^8$, wherein $R^8$ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl and m represents the number 0, 1 or 2, $X^1$ represents oxygen or sulphur, A represents a bridge member of the formula

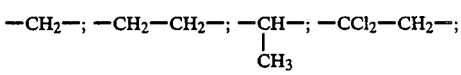

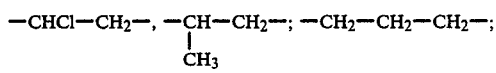

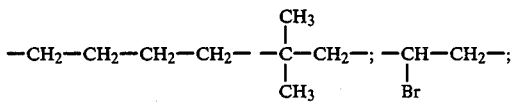

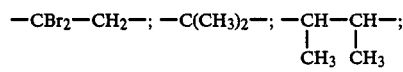

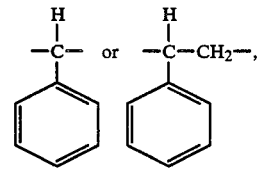

n represents the number 0 or 1 and $X^2$ represents oxygen or represents a radical =N—O—$R^4$, or represents a radical

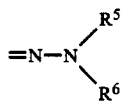

wherein $R^4$ represents hydrogen, or represents straight-chain or branched alkyl with 1 to 6 carbon atoms, or represents in each case straight-chain or branched alkenyl or alkinyl with in each case 3 to 6 carbon atoms, or represents in each case straight-chain or branched halogenoalkyl with 1 to 6 carbon atoms or halogenoalkenyl with 3 to 6 carbon atoms and in each case 1 to 5 identical or different halogen atoms, or represents in each case straight-chain or branched alkoxyalkyl or alkylthioalkyl with in each case 1 to 3 carbon atoms in the individual alkyl parts, or represents benzyl, phenethyl or phenyl, in each case mono-, di-, tri-, tetra- or pentasubstituted by identical or different substituents in the phenyl part by substituents selected from the group consisting of fluorine, chlorine, bromine, iodine, cyano, nitro, methyl, ethyl, n- or i-propyl, n-, i-, s- or t-butyl, methoxy and ethoxy, $R^5$ represents hydrogen, or represents straight-chain or branched alkyl with 1 to 4 carbon atoms and $R^6$ represents hydrogen, or represents straight-chain or branched alkyl with 1 to 4 carbon atoms, or reoresents phenyl which is optionally mono-, di-, tri-, tetra- or pentasubstituted by identical or different substituents, or represents a radical

possible substituents on the phenyl being those mentioned for $R^4$, $X^3$ represents oxygen or sulphur and $R^7$ represents hydrogen, or represents straight-chain or branched alkyl with 1 to 6 carbon atoms, or represents in each case straight-chain or branched alkoxy, alkylamino or dialkylamino with in each case 1 to 4 carbon atoms in the individual alkyl parts.

3. A compound according to claim 1 wherein such compound is 4-nitro-5-methoxyimino-acetyl-amino-1-(2,6-dichloro-4-trifluoromethylphenyl)-pyrazole of the formula

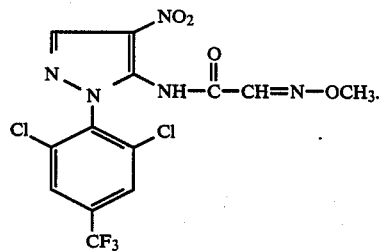

4. A compound according to claim 1 wherein such compound is 4-nitro-5-methoximinoacetyl-amino-1-(2,3,5,6-tetrafluoro-4-trifluoromethylphenyl)-pyrazole of the formula

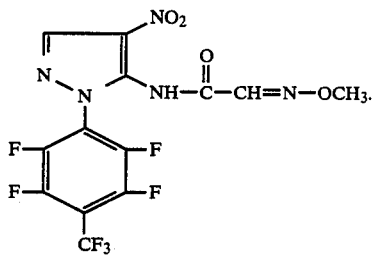

5. A compound according to claim 1 wherein such compound is 4-nitro-5-methoximino-acetyl-amino-1-(2-chloro-6-fluoro-4-trifluorpmethylphenyl)pyrazole of the formula

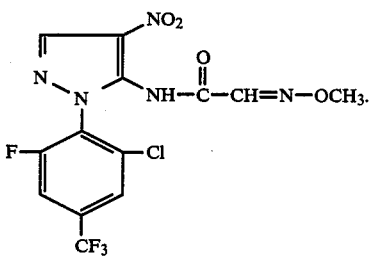

6. A compound according to claim 1 wherein such compound is 4-nitro-5-methoximino-acetyl-amino-1-(2,6-dichloro-3-fluoro-4-trifluoromethylphenyl)-pyrazole of the formula

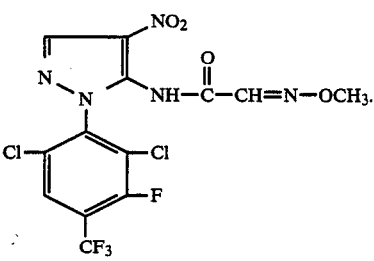

7. A herbicidal composition comprising a herbicidally effective amount of a 5-acylamino-pyrazole derivative according to claim 1 and a diluent.

8. A method of combating unwanted vegetation which comprises applying to such vegetation or to a locus from which it is desired to exclude such vegetation a herbicidally effective amount of a 5-acylaminopyrazole derivative according to claim 1.

9. The method according to claim 8 wherein such 5-acylamino-pyrazole derivative is
4-nitro-5-methoximino-acetyl-amino-1-(2,6-dichloro-4-trifluoromethylphenyl)-pyrazole,
4-nitro-5-methoximinoacetyl-amino-1-(2,3,5,6-tetrafluoro-4-trifluoromethylphenyl)-pyrazole,
4-nitro-5-methoximino-acetyl-amino-1-(2-chloro-6-fluoro-4-trifluoromethylphenyl)-pyrazole or
4-nitro-5-methoximino-acetyl-amino-1-(2,6-dichloro-3-fluoro-4-trifluoromethylphenyl)-pyrazole.

* * * * *

UNITED STATES PATENT AND TRADEMARK OFFICE
CERTIFICATE OF CORRECTION

PATENT NO. : 4,799,951

DATED : January 24, 1989

INVENTOR(S) : Jörg Stetter, et al

Page 1 of 2

It is certified that error appears in the above-identified patent and that said Letters Patent is hereby corrected as shown below:

| | |
|---|---|
| Abstract, line 16 | Delete "0 to 1" and substitute --0 or 1-- |
| Title Page, Title, line 2, and Col. 1, line 2 | After "THEM" insert --,-- |
| Col. 5, line 67 | Delete "4pyridyl" and substitute --4-pyridyl-- |
| Col. 9, line 60 | Delete entire line and substitute -- -$CH_2$-; -$CH_2$-$CH_2$-; -$CH_2$-$CH_2$-$CH_2$-; -CH-; -- <br>                                   $CH_3$ |
| Col. 31, lines 67-68 | Correct spelling of --represented-- |
| Col. 42, line 41 | Start new paragraph with "Mixtures" |
| Col. 43, line 2 | Delete "acar:cides" and substitute --acaricides-- |
| Col. 43, line 3 | Delete "wnich" and substitute --which-- |
| Col. 44, lines 53-54 | Correct --trifluoromethylphenyl-- |
| Col. 45, Example 9, under 4th column | Delete end of formula and substitute --N-$OCH_3$-- <br>                           ‖ <br>                       -C-$CH_3$ |
| Col. 53, line 36 | Before "damage" insert --%-- |
| Col. 54, line 29 | Correct --alkyl-- |
| Col. 54, line 29 | After "with" insert -- 1 -- |
| Col. 54, lines 36-37 | Delete "represented" and substitute --represents-- |
| Col. 54, line 60 | Delete "1to 4" and substitute --1 to 4-- |
| Col. 55, line 46 | Correct spelling of --substituents-- |

UNITED STATES PATENT AND TRADEMARK OFFICE
CERTIFICATE OF CORRECTION

PATENT NO. : 4,799,951

DATED : January 24, 1989

INVENTOR(S) : Jörg Stetter, et al

It is certified that error appears in the above-identified patent and that said Letters Patent is hereby corrected as shown below:

Col. 57, lines 30-31    Correct spelling of --represents--

Col. 57, line 48    Delete "methoxyimino" and substitute --methoximino--

Col. 58, line 17    Correct --trifluoromethylphenyl--

Signed and Sealed this

Fifth Day of December, 1989

Attest:

JEFFREY M. SAMUELS

Attesting Officer    Acting Commissioner of Patents and Trademarks